United States Patent
Gajula et al.

(10) Patent No.: US 11,084,764 B2
(45) Date of Patent: Aug. 10, 2021

(54) PROCESS FOR CATALYST ACTIVATION FOR LOWER ALKANE DEHYDROAROMATIZATION

(71) Applicant: SABIC GLOBAL TECHNOLOGIES B.V., Bergen op Zoom (NL)

(72) Inventors: Sreenivasarao Gajula, Bangalore (IN); Amit Kumar, Bangalore (IN); Ziyad Kottavarithottil, Bangalore (IN); Anshita Sudarshan, Bangalore (IN); Eswara Rao Mupparaju, Bangalore (IN); Suman Kumar Jana, Bangalore (IN); Anthonisamy Selvanathan, Bangalore (IN); Sivakumar Sreeramagiri, Bangalore (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/469,927

(22) PCT Filed: Dec. 28, 2017

(86) PCT No.: PCT/IB2017/058481
§ 371 (c)(1),
(2) Date: Jun. 14, 2019

(87) PCT Pub. No.: WO2018/122778
PCT Pub. Date: Jul. 5, 2018

(65) Prior Publication Data
US 2020/0239383 A1    Jul. 30, 2020

Related U.S. Application Data

(60) Provisional application No. 62/439,663, filed on Dec. 28, 2016.

(51) Int. Cl.
*C07C 2/76* (2006.01)
*B01J 29/48* (2006.01)
(Continued)

(52) U.S. Cl.
CPC ............... *C07C 2/76* (2013.01); *B01J 29/48* (2013.01); *B01J 37/18* (2013.01); *C10G 35/095* (2013.01);
(Continued)

(58) Field of Classification Search
CPC ........ C07C 2/76; C07C 2529/48; B01J 29/48; B01J 37/18; C10G 35/065; C10G 35/095;
(Continued)

(56) References Cited

U.S. PATENT DOCUMENTS 7,728,186 B2    6/2010    Iaccino et al.
7,893,308 B2    2/2011    Sangar et al.
(Continued)

FOREIGN PATENT DOCUMENTS

WO    2011144319 A1    11/2011
WO    WO-2011144319 A1 *  11/2011 ............... C07C 2/76

OTHER PUBLICATIONS

Bouchy et al., Journal of Molecular Catalysis A: Chemical 163 (2000) 283-296.
(Continued)

*Primary Examiner* — Youngsul Jeong
*Assistant Examiner* — Jason Y Chong
(74) *Attorney, Agent, or Firm* — Cantor Colburn LLP

(57) ABSTRACT

Described herein is a method for producing a zeolite catalyst useful for aromatization of a lower alkane, a zeolite catalyst useful for aromatization of a lower alkane obtainable by said method and a process for aromatization of a lower alkane using the zeolite catalyst.

17 Claims, 2 Drawing Sheets

(51) Int. Cl.
  *B01J 37/18* (2006.01)
  *C10G 35/095* (2006.01)
(52) U.S. Cl.
  CPC .. *C07C 2529/48* (2013.01); *C10G 2300/1081* (2013.01)
(58) Field of Classification Search
  CPC ...... C10G 2300/104; C10G 2300/1081; Y02P 20/52
  See application file for complete search history.

(56) References Cited

U.S. PATENT DOCUMENTS

| | | |
|---|---|---|
| 8,735,310 B2 | 5/2014 | Ma et al. |
| 2007/0249740 A1 | 10/2007 | Iaccino et al. |
| 2008/0249342 A1 | 10/2008 | Iaccino et al. |
| 2013/0066126 A1 | 3/2013 | Jana |
| 2016/0121314 A1 | 5/2016 | Jana |

OTHER PUBLICATIONS

Guil-Lopez et al., Journal of Solid State Chemistry 190 (2012) 285-295.
International Search Report for International Application No. PCT/IB2017/058481, International Filing Date Dec. 28, 2017, dated May 4, 2018, 5 pages.
Lacheen et al, Phys. Chem. Chem. Phys., 2005, 7, 538-547.
Liu et al., Kinetics and Catalysis, vol. 41, No. 1, 2000, pp. 132-144.
Ma et al., Journal of Natural Gas Chemistry, 14 (2005), 129-139.
Nagai et al., Applied Catalysis A: General 253 (2003) 101-112.
Post-synthesis Modification I; Molecular Sieves, vol. 3; Eds. H. G. Karge, J. Weitkamp; Year (2002); pp. 204-255.
Written Opinion for International Application No. PCT/IB2017/058481, International Filing Date Dec. 28, 2017, dated May 4, 2018, 8 pages.

\* cited by examiner

PROCESS FOR CATALYST ACTIVATION FOR LOWER ALKANE DEHYDROAROMATIZATION

CROSS REFERENCE TO RELATED APPLICATIONS

This application is a National Stage application of PCT/IB2017/058481, filed Dec. 28, 2017, which claims the benefit of U.S. Provisional Application No. 62/439,663, filed Dec. 28, 2016, both of which are incorporated herein by reference in their entirety.

BACKGROUND

It has been previously described that lower alkanes can be directly converted into higher hydrocarbons using a molybdenum-modified medium pore-size zeolite catalyst.

A drawback of the use of molybdenum-modified zeolite catalyst for the aromatization of lower alkanes is that coke is deposited on the catalyst surface which reduces catalyst activity. Attempts to reduce coke formation has met with some success but further improvement is needed.

BRIEF DESCRIPTION

Disclosed herein is a method for producing a zeolite catalyst useful for aromatization of a lower alkane comprising: contacting a molybdenum modified zeolite catalyst precursor with a gas stream comprising a lower alkane and a reducing gas at a first temperature of 40° C. to 250° C. that is increased to a second temperature of greater than 250° C. to 750° C. at a rate of less than 5° C./minute to yield an activated zeolite catalyst.

A method for aromatization of a lower alkane comprises contacting the zeolite catalyst produced by the method described above with a feed stream comprising a lower alkane under aromatization conditions.

The above described and other features are exemplified by the following figures and detailed description.

BRIEF DESCRIPTION OF THE DRAWINGS

The following figures are exemplary embodiments wherein the like elements are numbered alike.

DETAILED DESCRIPTION

Figure 1:
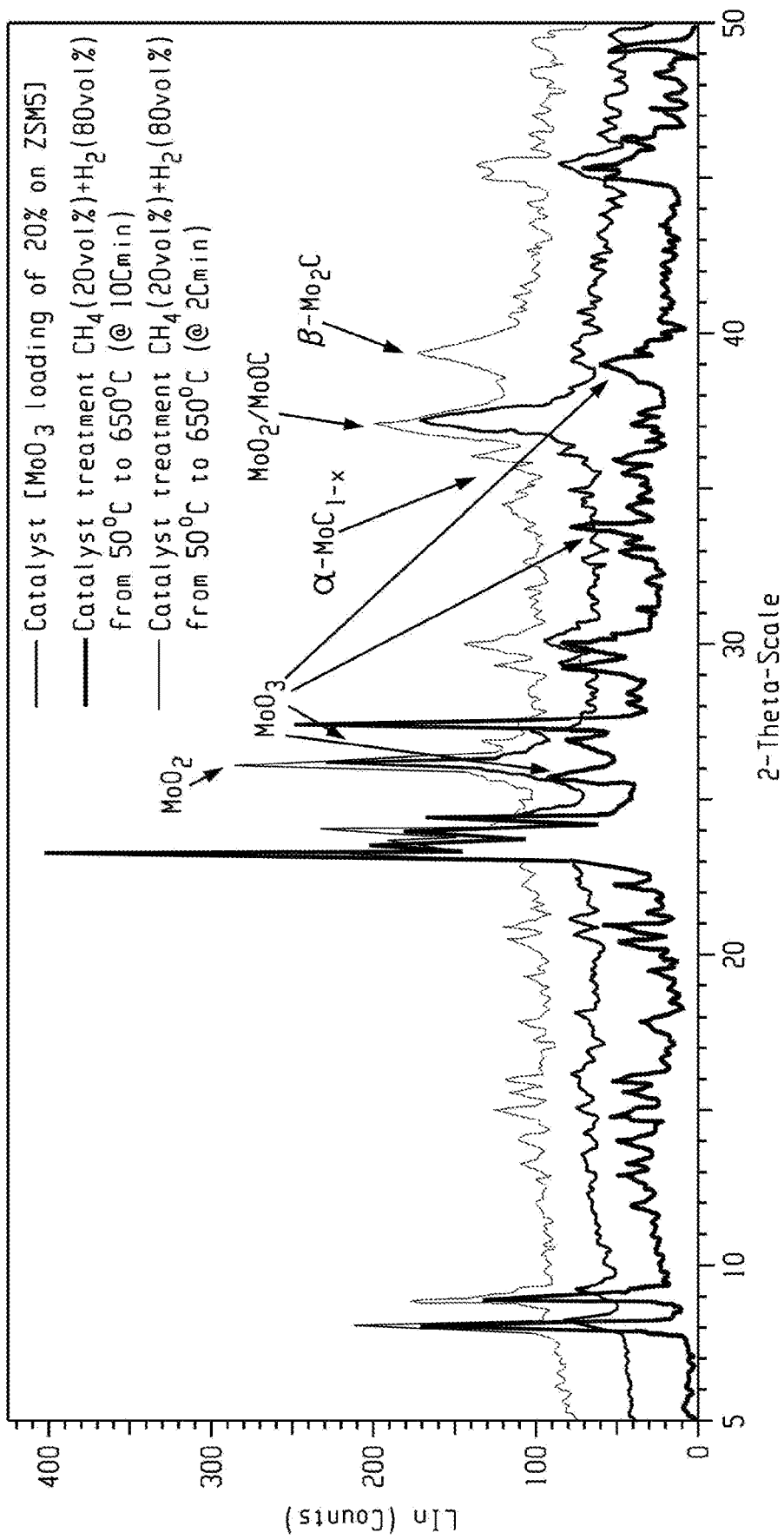
FIG. 1 is a graphical representation of x-ray diffraction data from the examples.

It was found that the pre-carburization of molybdenum modified zeolite catalyst precursor with a combined stream of a lower alkane methane and reducing gas at a constantly increasing temperature e.g. from initial temperature to a temperature useful for aromatization (750° C.) remarkably improves the stability/performance of the catalyst for lower alkane aromatization. Moreover, it was found that catalyst performance is even further improved when the rate of temperature increase is less than 5° C./minute.

The term "zeolite catalyst precursor" or "catalyst precursor" as used herein relates to the zeolite-based composition at any stage prior to the pre-carburizing step as described herein.

Prior to the pre-carburization step, the zeolite catalyst precursor comprises 2-10 weight percent (wt %) molybdenum (Mo), or 3-5 wt % Mo, based on the total weight of the catalyst precursor. In addition, the zeolite catalyst precursor may further contain 0.1-2 wt % of one or more additional elements selected from Group 6-11 of the Periodic Table (IUPAC version of 22 Jun. 2007). In some embodiments, the one or more additional elements may be selected from Group 6-10 of the Periodic Table. Exemplary additional elements include tungsten (W), platinum (Pt), ruthenium (Ru), rhenium (Re), cobalt (Co), copper (Cu) and iron (Fe). Methods useful for determining the quantity of Mo and other elements comprised in the compositions as described herein are well known in the art and include AAS (Atomic Absorption Spectrometer) or ICP (Inductively Coupled Plasma Spectrometry) analysis.

The aluminosilicate zeolite is a medium-pore size zeolite having a pore size of 4 to 8 angstroms (Å), or 5 to 7 Å, or 5-6 Å. Exemplary medium-pore size zeolites are 10-ring zeolites; i.e. the pore is formed by a ring consisting of 10 $SiO_4$ tetrahedra. In some embodiments, the zeolite is of the pentasil type. The zeolite may be H-ZSM-5. Other zeolites that can be used for lower alkane aromatization include, but are not limited to, MCM-22 and H-ZSM-11.

In some embodiments, the zeolite is in the hydrogen form: i.e. having at least a portion of the original cations associated therewith replaced by hydrogen. Methods to convert an aluminosilicate zeolite to the hydrogen form include direct ion exchange employing an acid and base exchange followed by calcination.

The zeolite may be dealuminated. Accordingly, the zeolite may have a Si/Al ratio of 10-50. Means and methods to obtain a dealuminated zeolite include, but are not limited to, the acid leaching technique; see e.g. Post-synthesis Modification I; Molecular Sieves, Volume 3; Eds. H. G. Karge, J. Weitkamp; Year (2002); Pages 204-255. In some embodiments using a dealuminated H-ZSM-5 zeolite having a Si/Al ratio of 10 to 50, or 10 to 20, or, 11 to 18, improves the performance/stability of the catalyst. Means and methods for quantifying the Si/Al ratio of a dealuminated zeolite include, but are not limited to, AAS (Atomic Absorption Spectrometer) or ICP (Inductively Coupled Plasma Spectrometry) analysis.

The zeolite catalyst precursor may be produced by various methods. For example, the zeolite catalyst precursor may be produced by a method comprising depositing Mo and optionally one or more additional elements selected from Group 6-11 of the Periodic Table on the zeolite using an incipient wetness method which comprises the steps of contacting a zeolite with a solution comprising a soluble Mo-salt and optionally a solution comprising one or more additional elements selected from Group 6-11 of the Periodic Table; and drying the zeolite to provide a zeolite catalyst precursor. When one or more additional elements are deposited, it is preferred that Mo is deposited first. Deposition of metal(s) onto the zeolite may also be carried out by using impregnation technique in aqueous solution under acidic as well as basic conditions. In some embodiments, the impregnation technique comprises using an aqueous solution of ammonium heptamolybdate at a pH of 9 to 11, or, 9.5 to 10.5. In one embodiment, the zeolite catalyst precursor is dried in air.

After drying, the catalyst precursor on which Mo and the optional additional element(s) are deposited is calcined in air, preferably in moisture free air. For example, the catalyst precursor is calcined at 500-650° C. and a pressure of 1 atmosphere (atm) for 1-5 hours. More specifically, the catalyst precursor may be calcined at 600° C. for 2 hours.

The zeolite catalyst useful for aromatization of a lower alkane can be made by a method comprising: contacting a molybdenum modified zeolite catalyst precursor with a gas stream comprising a lower alkane and a reducing gas at a first temperature of 40° C. to 250° C. and increasing the temperature to a second temperature of greater than 250° C. to 750° C. at a rate of less than 5° C./minute to yield an activated zeolite catalyst.

The gas stream comprising a lower alkane and a reducing gas is sometimes referred to as "pre-carburizing gas stream." The term "pre-carburizing gas stream" as used herein relates to a gas stream comprising a 5 to 30 volume percent (vol %) lower alkane and 70-95 vol % of a reducing gas. The term "reducing gas" as used herein relates to an element or compound (or a mixture thereof) which is gaseous at the conditions used for pre-carburization and which is capable of reducing the molybdenum compounds on the catalyst. An exemplary gas is hydrogen ($H_2$). The gas stream may further comprise at least one of an inert gas such as nitrogen ($N_2$), helium (He), argon (Ar). The maximum allowable amount of other components like an inert gas in the pre-carburizing gas stream is 10 vol %, specifically up to 5 vol % and more specifically up to 2 vol %. The pre-carburizing gas stream may consist essentially of lower alkane and a reducing gas (i.e. less than 1 vol % of other components).

The temperature is increased from a first temperature (i.e. 40° C.-250° C.) to a temperature useful for aromatization. The first temperature may be 50=70° C., or, 100-250° C. The temperature is increased at a rate that is less than 5° C./minute, or, less than or equal to 3° C./minute, or, less than or equal to 2° C./minute. The second temperature may be 600 to 850° C., or, 600 to 750° C., or, 600° C. to 700° C., or 700-750° C.

The temperature useful for aromatization can be easily determined by the person skilled in the art; see e.g. Ismagilov (2008) Energy and Environmental Science 526-541. For example, the temperature useful for aromatization may be 600-850° C., or, 725-800° C., or, 700-750° C. The pressure at which the aromatization reaction is carried out may be 0.2-5 atmosphere (atm), or, 0.5-2 atm.

When the temperature useful for aromatization is reached, the temperature may be kept constant for a certain period of time before, for instance, switching the gaseous feed of the catalyst from the pre-carburization stream to a feed stream for aromatization. For example, the temperature is kept constant for 5-60 minutes at the temperature useful for aromatization after attaining said temperature useful for aromatization. More specifically, the temperature may be kept constant for 15 minutes at the temperature useful for aromatization after attaining said temperature useful for aromatization. In some embodiments, the aromatization reaction is started immediately after the pre-carburization. However, it is possible to cool down the catalyst after pre-carburization and then to later directly use the catalyst without having to redo the pre-carburization.

Accordingly, the zeolite catalyst produced by the method described herein is useful in a process for converting a feed stream comprising a lower alkane to a product stream comprising aromatic hydrocarbons. This process for converting a lower alkane to aromatic hydrocarbons is also described herein as "lower alkane aromatization". A lower alkane is defined as having four carbons or less. In some embodiments, the "lower alkane" is methane ($CH_4$), ethane ($C_2H_5$) or a mixture thereof. In some embodiments the mixture comprises up to 20 mole-% ethane in methane. In some embodiments the "lower alkane" is methane ($CH_4$). The aromatic hydrocarbons produced by the lower alkane aromatization process include benzene, toluene and xylenes (commonly denoted as "BTX").

More specifically, a process for aromatization of a lower alkane comprises contacting the catalyst with a feed stream comprising a lower alkane at conditions useful for aromatization. As used herein, the term "feed stream" relates to the gaseous stream which is brought into contact with the catalyst to convert the therein comprised lower alkane into aromatic hydrocarbons. In one embodiment, the feed stream is different from the pre-carburizing gas stream in that it e.g. does not comprise a reducing gas. In some embodiments, the feed stream consists of lower alkane, or, 0-20 mole % ethane in methane, or, more specifically, the feed stream consists of pure methane.

The invention will now be more fully described by the following non-limiting Examples.

EXAMPLES

X-RAY DIFFRACTION ANALYSIS: X-ray diffraction (XRD) technique was used to understand the structural changes in catalysts during carburization. Usually, 5 wt % loading of Mo on H-ZSM-5 is prepared as catalyst material but this material is not traceable by XRD. Hence a separate bulk type material with a Mo loading of 20 wt % on H-ZSM5 was prepared and subjected to XRD analysis. The catalysts with 20 wt % Mo on H-ZSM5 were subjected to carburization with a feed at a certain fixed flow (1,000-10,000 milliliters per gram per hour (ml/g/Hr)) of a mixture of $CH_4$ (20 vol %)+$H_2$ (80 vol %) from 50° C. to 650° C. at heating rates of 2° C./min and 10° C./min. Results are shown in FIG. 1.

Studies by XRD revealed $MoO_3$ structure and identified formation of α and β molybdenum carbide phases upon carburization of Mo (20 wt %) on H-ZSM5 under the above carburization conditions.

Figure 2:
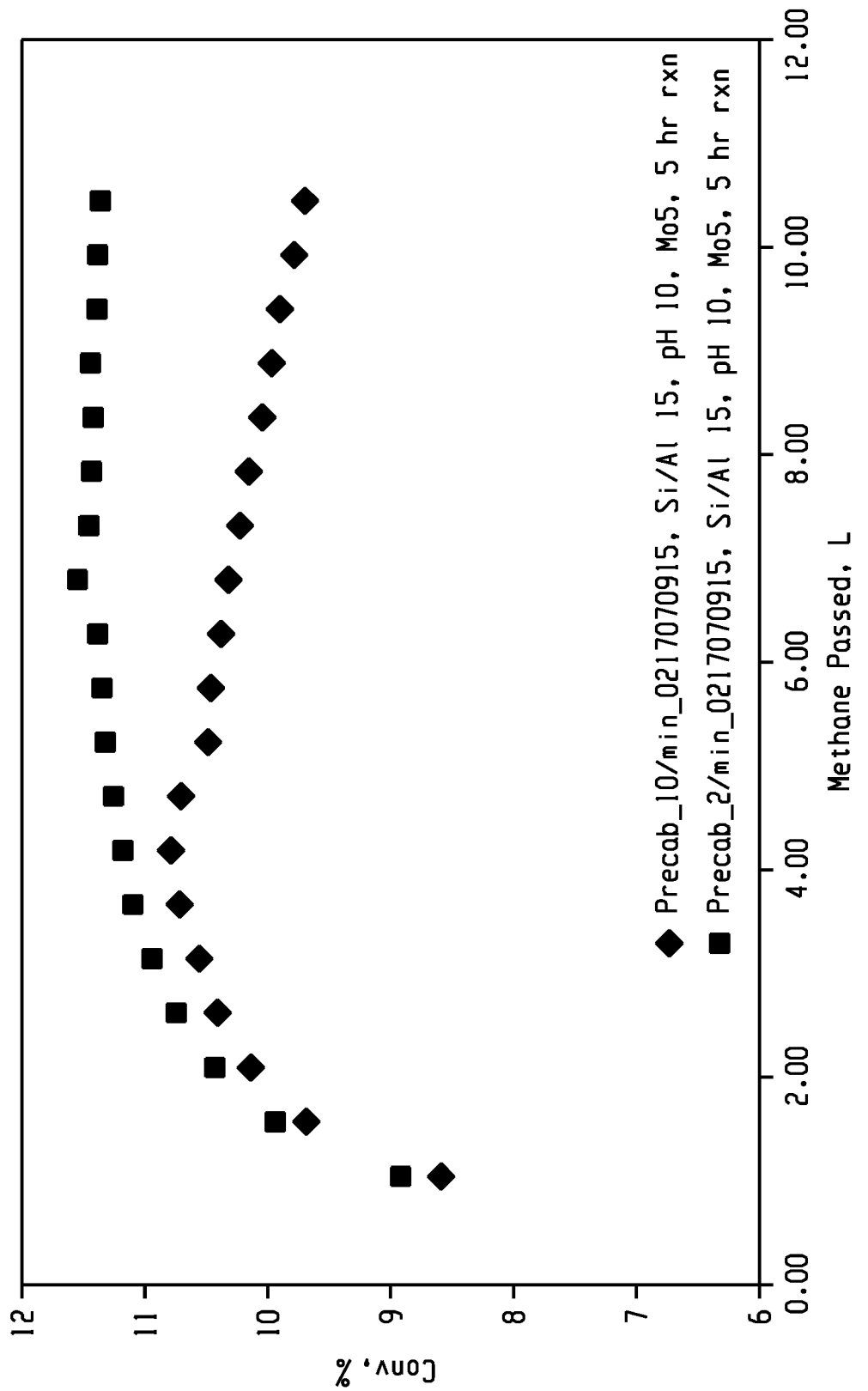
FIG. 2 is a graphical representation of reaction conversion data from the examples.

DEHYDROAROMATIZATION: Methane dehydro aromatization reaction was carried out using molybdenum loaded H-ZSM-5 catalyst (5 wt % Mo) at atmospheric pressure at 725° C. and 1,050 ml/g/hr conditions using a methane feed stream. The catalyst was pre-reduced in-situ by molybdenum oxide carburization with a feed mixture of $CH_4$ (20 vol %)+$H_2$ (80 vol %) from 50° C. to 650° C. at heating rates of 2° C./min and 10° C./min at a flow rate equivalent to 1,050 ml/g/hr. The reaction was carried out and methane conversion data on two catalysts carburized at different rates is presented in FIG. 2. The data clearly indicates the superior performance of the catalyst carburized at a heating rate of 2° C./minute over a faster heating rate of 10° C./minute.

This disclosure further encompasses the following embodiments.

Embodiment 1

A method for producing a zeolite catalyst useful for aromatization of a lower alkane comprising: contacting a molybdenum modified zeolite catalyst precursor with a gas stream comprising a lower alkane and a reducing gas at a first temperature of 40° C. to 250° C. that is increased to a second temperature of greater than 250° C. to 750° C. at a rate of less than or equal to 5° C./min to yield an activated zeolite catalyst.

Embodiment 2

The method of Embodiment 1, wherein the temperature increases at a rate less than or equal to 3° C./min.

Embodiment 3

The method of any one of Embodiments 1-2, wherein the temperature increases at a rate of less than or equal to 2° C./min.

Embodiment 4

The method of any one of Embodiments 1-3, wherein the gas stream comprises 5 vol. % to 30 vol. % of the lower alkane.

Embodiment 5

The method of any one of Embodiments 1-4, wherein the lower alkane comprises methane.

Embodiment 6

The method of any one of Embodiments 1-5, wherein the molybdenum modified zeolite catalyst precursor comprises H-ZSM-5.

Embodiment 7

The method of any one of Embodiments 1-6, wherein the molybdenum modified zeolite catalyst precursor further comprises 0.1 wt. % to 2 wt. % of an additional element selected from the Groups 6-11 of the Periodic Table.

Embodiment 8

The method of any one of Embodiments 1-7, wherein the reducing gas comprises hydrogen.

Embodiment 9

The method of any one of Embodiments 1-8, wherein the gas stream comprises 70-95 vol. % of the reducing gas.

Embodiment 10

The method of any one of Embodiments 1-9 wherein the first temperature is from 50 to 70° C., the second temperature is 600 to 700° C., and the rate is 1° C./min to 3° C./min.

Embodiment 11

The method of any one of Embodiments 1-10, wherein the gas activated zeolite catalyst has a Si/Al ratio of 10 to 20, or, 11 to 18.

Embodiment 12

The method of any one of Embodiments 1 to 11, wherein an inert gas is present in an amount less than or equal to 10 vol. %, based on the total volume of the gas stream.

Embodiment 13

The method of any of Claims 1-12 wherein the zeolite catalyst precursor comprises 2 wt. % to 10 wt. % molybdenum, based on the total weight of the precursor.

Embodiment 14

The method of Claim 13, wherein the zeolite precursor comprises 3 wt. % to 5 wt. % molybdenum, based on the total weight of the precursor.

Embodiment 15

A zeolite catalyst for aromatization of a lower alkane obtainable by the method of any one of Claims 1-14.

Embodiment 16

A method for aromatization of a lower alkane comprising: contacting the zeolite catalyst produced by the method of any of Claims 1-14 with a feed stream comprising a lower alkane under aromatization conditions.

Embodiment 17

The method of Embodiment 16, wherein the feed stream comprises methane.

Embodiment 18

The method of Claim 16, wherein the feed stream consists of methane.

Embodiment 19

The method of any of Embodiments 16-18, wherein aromatization conditions comprise a temperature of 600 to 850° C.

Embodiment 20

The method of Embodiment 19, wherein aromatization conditions comprise 0.5 to 2 atm at a temperature of 725 to 800° C.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for producing a zeolite catalyst useful for aromatization of a lower alkane comprising:
   contacting a molybdenum modified zeolite catalyst precursor with a gas stream comprising (i) a first lower alkane and (ii) a reducing gas at a first temperature of 50° C. to 70° C. that is increased to a second temperature of 600° C. to 700° C. at a rate of 1° C. /min to 3° C. /min to yield an activated zeolite catalyst, and
   wherein the gas stream comprises the reducing gas in an amount of 70-95 vol.%, based on a total volume of the gas stream.

2. The method of claim 1, wherein the gas stream further comprises an inert gas in an amount of 2 vol.% to 5 vol.%, based the total volume of the gas stream.

3. The method of claim 1, wherein the first temperature is increased to the second temperature at a rate of 1° C. /min to 2° C. /min.

4. The method of claim 1, wherein the gas stream comprises the first lower alkane in an amount of 5 vol.% to 30 vol.%, based on the total volume of the gas stream.

5. The method of claim 1, wherein the first lower alkane comprises methane.

6. The method of claim 1, wherein the molybdenum modified zeolite catalyst precursor comprises H-ZSM-5.

7. The method of claim 1, wherein the molybdenum modified zeolite catalyst precursor further comprises 0.1 wt.% to 2 wt.% of an additional element selected from the Groups 6-11 of the Periodic Table.

8. The method of claim 1, wherein the reducing gas comprises hydrogen.

9. The method of claim 1, wherein the activated zeolite catalyst has a Si/Al ratio of 10 to 20, or, 11 to 18.

10. The method of claim 1, wherein the gas stream further comprises an inert gas in an amount greater than 0 vol.% to 10 vol.%, based on the total volume of the gas stream.

11. The method of claim 1, wherein the molybdenum modified zeolite catalyst precursor comprises 2 wt.% to 10 wt.% molybdenum, based on a total weight of the molybdenum modified zeolite catalyst precursor.

12. The method of claim 11, wherein the molybdenum modified zeolite catalyst precursor comprises 3 wt.% to 5 wt.% molybdenum, based on a total weight of the molybdenum modified zeolite catalyst precursor.

13. A method for aromatization of a lower alkane comprising:
   contacting a molybdenum modified zeolite catalyst precursor with a gas stream comprising (i) a first lower alkane and (ii) a reducing gas at a first temperature of 50° C. to 70° C. that is increased to a second temperature of 600° C. to 700° C. at a rate of 1° C. /min to 3° C. /min to yield an activated zeolite catalyst, wherein the gas stream comprises the reducing gas in an amount of 70-95 vol.%, based on a total volume of the gas stream; and
   contacting the activated zeolite catalyst with a feed stream comprising a second lower alkane under aromatization conditions to produce a product stream comprising an aromatic hydrocarbon.

14. The method of claim 13, wherein the feed stream comprises methane.

15. The method of claim 13, wherein the feed stream consists of methane.

16. The method of claim 13, wherein aromatization conditions comprise a temperature of 600 to 850° C.

17. The method of claim 16, wherein aromatization conditions comprise 0.5 to 2 atm at a temperature of 725 to 800° C.

* * * * *